United States Patent [19]

Reese et al.

[11] 4,010,253
[45] Mar. 1, 1977

[54] PROCESS OF SUPPRESSING ODORS EMPLOYING DEODORANTS CONTAINING ESTERS OF CITRIC ACID

[75] Inventors: Günter Reese, Dusseldorf-Holthausen; Rainer Osberghaus, Dusseldorf-Urdenbach, both of Germany

[73] Assignee: Henkel & Cie G.m.b.H., Dusseldorf-Holthausen, Germany

[22] Filed: Apr. 2, 1975

[21] Appl. No.: 564,555

[30] Foreign Application Priority Data

Apr. 16, 1974 Germany .......................... 2418338

[52] U.S. Cl. ............................. 424/47; 424/DIG. 5; 424/69
[51] Int. Cl.² .......................................... A61K 7/32
[58] Field of Search ...................... 424/46, 313, 47

[56] References Cited

UNITED STATES PATENTS 3,124,506  3/1964  Holman ........................... 424/65 X
3,198,828  8/1965  Matter ............................. 424/65 X
3,833,720  9/1974  Crotty et al. ........................ 424/47

FOREIGN PATENTS OR APPLICATIONS 2,225,313  12/1972  Germany ........................... 424/47

OTHER PUBLICATIONS

Neurath et al., 1968, vol. 69, pp. 1832j, Chem. Abs.
Bomar Chem. Abs., 1968, vol. 69, pp. 67994v.

Primary Examiner—Dale R. Ore
Attorney, Agent, or Firm—Hammond & Littell

[57] ABSTRACT

A process of suppressing body odor comprising applying a substantially anhydrous cosmetic preparation for suppressing body odor containing as a deodorant an ester of citric acid or acetylcitric acid with an aliphatic alcohol having from 1 to 6 carbon atoms or an alicyclic alcohol having 5 to 6 atoms.

6 Claims, No Drawings

PROCESS OF SUPPRESSING ODORS EMPLOYING DEODORANTS CONTAINING ESTERS OF CITRIC ACID

It is known that the troublesome odor which accompanies human perspiration is caused by the bacterial decomposition of the initially odorless perspiration. There have therefore been numerous suggestions for ways of overcoming this difficulty, but no universally satisfactory solution has hitherto been found. Basically two methods of solving this problem have been proposed. Firstly, the use of anti-microbial compounds for killing the bacterial skin flora which cause the decomposition of the perspiration, and secondly, the use of compounds which prevent the secretion of perspiration. In addition to the above agents, compositions which have a purely absorptive action and which mask the odor are of lesser importance. In contrast to the anti-perspirants, the cosmetic compositions which have a deodorizing action without exception contain antimicrobial substances.

The following are examples of substances which have been proposed and, in some cases, used in deodorant compositions: phenol derivatives with and without halogen substituents, organic mercury compounds, quaternary ammonium compounds and derivatives of amino acids having a disinfectant action. Even though the risk of skin irritations is not as great when deodorants are used as when anti-perspirants are used; nevertheless, various degrees of incompatibility, sensitivity with respect to light and toxic side effects do occur periodically when deodorants containing antimicrobial agents are used constantly. Furthermore, the majority of these products are not odorless and many have a slight phenolic odor. Attempts have therefore also been made to produce cosmetic compositions which are very good deodorants, are neutral with respect to odor and are largely free from side effects.

It is an object of the present invention to provide a process of suppressing body odor comprising applying a substantially anhydrous cosmetic preparation for suppressing body odor containing as a deodorant an ester of citric acid or acetylcitric acid with an aliphatic alcohol having from 1 to 6 carbon atoms or an alicyclic alcohol having 5 to 6 carbon atoms.

Another object of the invention is to provide a substantially anhydrous cosmetic composition for suppressing body odor containing as a deodorant, from about 1 to 25% by weight of at least one of the above esters.

These and further objects of the present invention will become apparent as the description thereof proceeds.

The present invention relates to the process of using cosmetic preparations for suppressing body odor which contain a deodorant and the process of suppressing body odor by applying the same to the body.

It has been found that the said requirements are substantially fulfilled by the use of esters of citric acid and/or acetylcitric acid with aliphatic alcohols having 1 to 6 carbon atoms in the molecules, or alicyclic alcohols having 5 to 6 carbon atoms in the molecule, as deodorants in anhydrous cosmetic preparations for the suppression of body odor.

According to the present invention there is provided a substantially anhydrous cosmetic preparation for the suppression of body odor containing as a deodorant an ester of citric acid and/or an ester of acetylcitric acid with an aliphatic alcohol having from 1 to 6 carbon atoms, or an alicyclic alcohol having from 5 to 6 carbon atoms.

More particularly, the present invention provides a process for suppressing body odor in a warm-blooded animal comprising applying topically to said warm-blooded animal an effective deodorizing amount of at least one citrate ester of an acid selected from the group consisting of citric acid and acetylcitric acid with an alcohol selected from the group consisting of alkanols having from 1 to 6 carbon atoms, cycloalkanols having from 5 to 6 carbon atoms and alkanepolyols having 2 to 6 carbon atoms and 2 to 6 hydroxy groups, and the remainder of inert cosmetic ingredients.

It is desirable that the cosmetic preparations of this invention be free from water for the reason of stability during the storage of such agents. In special cases, however, water contents of up to 5% can be tolerated, depending on the ester used and the stability requirements. Such preparations containing little water are regarded as substantially anhydrous within the meaning of the present invention.

The esters of citric acid to be used according to the invention can be prepared in known way by azeotropic esterification of citric acid with the respective alcohol, as described, for example, for triethyl citrate in the U.S. Pat. No. 2,076,111 (referred to in Chem. Zentralblatt, 1937, II, page 665). The preparation of the acetylcitric acid esters to be used according to the invention may be effected by reacting the corresponding citric acid ester with acetyl chloride, as described for the acetylcitric acid triethyl ester by Wislicenus in Liebigs Annalen der Chemie, Vol. 129, page 192, or by reacting the corresponding citric ester with acetic anhydride, as described likewise for the triethyl ester of acetylcitric acid in U.S. Pat. No. 2,445,911 (referred to in Chemical Abstracts, 1948, column 8818).

Examples of suitable esterifying aliphatic or alicyclic alcohols include alkanols having 1 to 6 carbon atoms such as methanol, ethanol, propanol, isopropanol, butanol-1, butanol-2, 2-methylpropanol-1, 2-methylpropanol-2, 2-methylbutanol-1, 2-methylbutanol-4 and n-hexylalcohol. Also included are alkanediols having 2 to 6 carbon atoms such as ethyleneglycol, propyleneglycol, trimethyleneglycol and hexamethyleneglycol, and alkanetriols having 3 to 6 carbon atoms such as glycerine, alkanetetrols having 4 to 6 carbon atoms such as erythritol, and alkanehexols having 4 to 6 carbon atoms such as sorbitol, and cycloalkanols having 5 to 6 carbon atoms such as cyclohexanol.

Among the citric acid esters and also the acetylcitric acid esters to be used in this invention the respective triesters are of the greatest importance, preferably those with alkanols having 1 to 6 carbon atoms in the molecule, both from the deodorizing action and the suitability for technical application.

Citric acid and acetylcitric acid esters to be used according to this invention are therefore, for example, monomethyl citrate, monoethyl citrate, monopropyl citrate, monoisopropyl citrate, mono-n-butyl citrate, mono-tert.-butyl citrate, monoamyl citrate, monohexyl citrate, monocyclohexyl citrate, monoglyceryl monocitrate, dimethyl citrate, diethyl citrate, dipropyl citrate, diisopropyl citrate, dibutyl citrate, dicyclohexyl citrate, the ester of 1 mol of citric acid with 2 mols of propylene glycol, monomethyl acetylcitrate, monoethyl acetylcitrate, monopropyl acetylcitrate, monobutyl acetylcitrate, monoamyl acetylcitrate, monocyclohexyl acetylcitrate, dimethyl acetylcitrate, diethyl acetylcitrate, diisopropyl acetylcitrate, di-tert.-butyl acetylcitrate, dihexyl acetylcitrate, the ester of 1 mol of acetylcitric acid with 2 mols of ethylene glycol, the ester of 1 mol of acetylcitric acid with 2 mols of hexamethylene glycol, the ester of 1 mol of citric acid with 3 mols of propylene glycol, the ester of 1 mol of acetylcitric acid with 3 mols of propylene glycol; but preferably, trimethyl citrate, triethyl citrate, tripropyl citrate, triisopropyl citrate, tri-n-butyl citrate, triamyl citrate, trihexyl citrate, trimethyl acetylcitrate, triethyl acetylcitrate, tripropyl acetylcitrate, triisopropyl acetylcitrate, tri-n-butyl acetylcitrate, tri-tert.-butyl acetylcitrate, triamyl acetylcitrate, and trihexyl acetylcitrate.

The citric acid or acetylcitric acid esters to be employed according to the inventon may be incorporated into all anhydrous preparations or substantially anhydrous preparations with a low water content, which are generally used as deodorants, and these include powders, pencils or sticks, roll-ons and sprays. The deodorant spray is the preferred embodiment of use. Incorporation is effected in a known manner, simply by stirring in or dissolving in the other constitutents of the preparation, namely inert cosmetic ingredients, such as solvents, waxes, fatty substances, polyglycols and powder bases. The amounts of citric acid esters or acetylcitric acid esters to be incorporated in the cosmetic composition or preparation with a deodorizing action according to the invention are from 1 to 25% by weight, preferably 5 to 15% by weight, based on the total weight of the preparation.

A sufficient amount of one of these preparations is applied topically to a warm-blooded animal to constitute an effective deodorizing amount for the suppression of body odor.

The citric acid ester or acetyl citric acid ester to be used according to the invention is preferably used as the sole deodorant substance but a combination with other deodorant substances is possible.

It is already known from various patent applications and patents, for example, the Specification (DOS) No. 2,137,924, German Patent No. 969,362 and U.S. Pat. No. 3,553,316, to use citric acid or its salts, combined with aluminum compounds or with anti-microbial agents in cosmetic preparations such as anti-perspirants. The citric acid or its salts, however, have no deodorizing action, but are added to these preparations on account of their antiseptic, astringent and bleaching properties. It is therefore very surprising that the esters of citric acid or acetylcitric acid with aliphatic alcohols having 1 to 6 carbon atoms, or alicyclic alcohols having 5 l to 6 carbon atoms, especially the corresponding triesters with alkanols having 1 to 6 carbon atoms, are marked by an exceptional deodorizing activity.

The following Examples further illustrate this invention without, however, it being restricted thereto.

EXAMPLES

Cosmetic compositions with a deodorant action according to the invention may be prepared according to the basic formulations given hereinafter. All parts are by weight unless otherwise indicated.

EXAMPLE 1

| Deodorant stick | Parts |
|---|---|
| 2-octyldodecanol | 26.0 |
| Cetyl/stearyl alcohol | 3.0 |
| Sodium stearate | 8.0 |
| Coconut fatty acid monoethanol amide | 3.0 |
| Paraffin oil | 2.0 |
| Propylene glycol | 2.0 |
| Ethanol | 48.5 |
| Tributyl citrate | 7.5 |

EXAMPLE 2

| Deodorant powder | Parts |
|---|---|
| Rice starch | 10.0 |
| Magnesium carbonate | 2.0 |
| Zinc oxide | 2.0 |
| Extra fine talcum | 76.0 |
| Tripropyl acetylcitrate | 10.0 |

EXAMPLE 3

| Deodorant spray | Parts |
|---|---|
| Triethyl citrate | 10.0 |
| Ethanol | 26.0 |
| Isopropanol | 2.8 |
| Propylene glycol | 1.2 |
| Propellant gas (Frigen 12/114) (dichlorodifluoromethane/dichlorotetrafluoroethane 60:40) | 60.0 |

EXAMPLE 4

| Deodorant spray | Parts |
|---|---|
| Triethyl acetylcitrate | 5.0 |
| Ethanol | 10.0 |
| Isopropanol | 18.0 |
| Isopropyl myristate | 2.0 |
| Propellant gas (Frigen 12/114) (dichlorodifluoromethane/dichlorotetrafluoroethane 60:40) | 65.0 |

EXAMPLE 5

| Deodorant spray | Parts |
|---|---|
| Tributyl citrate | 7.0 |
| Caprylic/capric acid triglyceride | 4.0 |
| Propellant gas (Frigen 12/114) (dichlorodifluoromethane/dichlorotetrafluoroethane 60:40) | 89.0 |

EXAMPLE 6

| Deodorant spray | Parts |
|---|---|
| Trimethyl citrate | 15.0 |
| Propylene glycol | 1.5 |
| Isopropyl stearate | 1.5 |
| Propellant gas (Frigen 12/114) (dichlorodifluoromethane/dichlorotetrafluoroethane 60:40) | 82.0 |

EXAMPLE 7

| Deodorant spray | Parts |
|---|---|
| Trihexyl citrate | 10.0 |
| Propylene glycol | 2.0 |
| Isopropyl myristate | 2.0 |
| Ethanol | 11.0 |
| Propellant gas (Frigen 11/12) (trichlorofluoromethane/dichlorodifluoromethane 50:50) | 75.0 |

EXAMPLE 8

| Deodorant spray | Parts |
|---|---|
| Tricyclohexyl acetylcitrate | 10.0 |
| Ethanol | 27.0 |
| Isopropyl myristate | 3.0 |
| Propellant gas (Frigen 12) (dichlorodifluoromethane) | 60.0 |

EXAMPLE 9

The following deodorant sprays were prepared for a comparative test of effectiveness.

| Deodorant Spray A (Invention) | Parts |
|---|---|
| Triethyl citrate | 5.0 |
| Isopropanol | 4.0 |
| Ethanol | 31.0 |
| Propellant gas (Frigen 12) (dichlorodifluoromethane) | 60.0 |

| Comparative Spray B | Parts |
|---|---|
| Citric acid | 5.0 |
| Isopropanol | 4.0 |
| Ethanol | 31.0 |
| Propellant gas (Frigen 12) (dichlorodifluoromethane) | 60.0 |

A test group consisting of 15 female and 15 male participants first of all used a soap F, which was free of antimicrobial agents, for a period of 5 days, with no deodorants or antiperspirants being used. Subsequently each participant was given a T-shirt and was instructed to treat one shoulder with the deodorant spray A on the morning of the sixth day after washing with soap F, and, for purposes of comparison, not to treat the other shoulder, one half of the group treating the left shoulder and the other half treating the right shoulder. The formation of odor was estimated by the test persons themselves and also by two cosmetic experts, by smelling the T-shirts after 8 hours and 24 hours. Subsequently, the test persons used soap F alone for a week. The test was then repeated, the hitherto untreated shoulder being treated with the deodorant spray and the other shoulder serving for comparison.

In both tests it was determined by all the persons taking part therein that the deodorant spray A prevented odor very well.

The test was repeated in a completely analogous procedure with the same test group, except that the only difference was that in each case comparative spray B was used instead of deodorant spray A. In this test, none of the participants could ascertain any significant reduction in odor.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:

1. A process for suppressing body odor in a warm-blooded animal comprising applying topically to said warm-blooded animal an effective deodorizing amount of a substantially anhydrous cosmetic preparation containing from 1 to 25% by weight based upon the total weight of at least one citrate ester of an acid selected from the group consisting of citric acid and acetylcitric acid with an alcohol selected from the group consisting of alkanol having from 1 to 6 carbon atoms, a cycloalkanol having from 5 to 6 carbon atoms and an alkanepolyol having 2 to 6 carbon atoms and 2 to 6 hydroxy groups; and the remainder of inert cosmetic ingredients.

2. The process of claim 1 wherein said citrate ester is esterified with 3 mols of said alcohol.

3. The process of claim 2 wherein said alcohol is an alkanol having from 1 to 6 carbon atoms.

4. The process of claim 1 wherein said preparation contains from 5 to 15% by weight based upon the total weight of said ester.

5. The process of claim 1 wherein said preparation contains a propellant gas and is applied topically by spraying as a deodorant spray.

6. A process for suppressing body odor in a warm-blooded animal comprising applying topically to said warm-blooded animal an effective deodorizing amount of at least one citrate ester of an acid selected from the group consisting of citric acid and acetylcitric acid with an alcohol selected from the group consisting of alkanol having from 1 to 6 carbon atoms, a cycloalkanol having from 5 to 6 carbon atoms and an alkanepolyol having 2 to 6 carbon atoms and 2 to 6 hydroxy groups.

* * * * *